United States Patent [19]

Wiskott et al.

[11] 4,071,630
[45] Jan. 31, 1978

[54] 1-SUBSTITUTED-AMINO-3-(4-FURO[3,2-c[PYRIDINYLOXY)-2-PROPANOLS

[75] Inventors: Erik Wiskott; Franz Troxler, both of Bottmingen, Switzerland

[73] Assignee: Sandoz Ltd., Basel, Switzerland

[21] Appl. No.: 733,565

[22] Filed: Oct. 18, 1976

Related U.S. Application Data

[63] Continuation-in-part of Ser. No. 605,972, Aug. 20, 1975, Pat. No. 3,998,835.

[30] Foreign Application Priority Data

Apr. 8, 1975 Switzerland ............ 4432/75

[51] Int. Cl.$^2$ ............ A61K 31/44; C07D 405/04
[52] U.S. Cl. ............ 424/256; 260/294.8 C; 260/294.9; 260/295 F; 260/296 H
[58] Field of Search ............ 260/296 H, 295 F, 294.9; 424/256

[56] References Cited

U.S. PATENT DOCUMENTS 3,705,907 12/1972 Troxler ............ 260/326.14R
3,751,429 8/1973 Seemann et al. ............ 260/326.14 R
3,845,065 10/1974 Shen et al. ............ 260/294.8 C Primary Examiner—Alan L. Rotman
Attorney, Agent, or Firm—Gerald D. Sharkin; Robert S. Honor

[57] ABSTRACT

This invention provides new compounds of formula I,

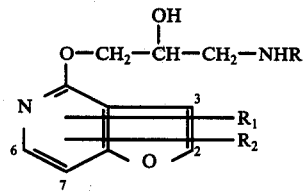

wherein
R is alkyl of 3 to 7 carbon atoms or cycloalkyl of 3 to 7 carbon atoms, cycloalkyl of 3 to 7 carbon atoms monosubstituted by alkyl of 1 to 4 carbon atoms, α-dialkylpropynyl of 5 to 9 carbon atoms or α-dialkyl-allyl of 5 to 9 carbon atoms, hydroxyalkyl of 2 to 7 carbon atoms or phenoxyalkyl of 8 to 11 carbon atoms, the oxygen atom of the last two radicals being separated by at least two carbon atoms from the nitrogen atom to which R is bound, $R_1$ is
 i. hydrogen or alkyl of 1 to 4 carbon atoms in the 2,3,6 or 7 position, or
 ii. chlorine or bromine, in the 2, 3 or 7 position,
 iii. nitro or —NHA wherein A is alkanoyl of 1 to 4 carbon atoms, in the 2, 3 or 7 position, or
 iv. fluorine, cyano or COOB, wherein B is alkyl of 1 to 4 carbon atoms, in the 2 or 3 position, and $R_2$ is
 i. hydrogen or alkyl of 1 to 4 carbon atoms in the 2, 3, 6 or 7 position,
 ii. chlorine or bromine, in the 2, 3 or 7 position, or
 iii. fluorine in the 2 or 3 position, useful in the treatment of heart diseases.

14 Claims, No Drawings

1-SUBSTITUTED-AMINO-3-(4-FURO[3,2-c]PYRIDINYLOXY)-2-PROPANOLS

This is a continuation-in-part of our copending application Ser. No. 605,972 filed Aug. 20, 1975 now U.S. Pat. No. 3,998,835, dated Dec. 21, 1976.

The present invention relates to new organic compounds.

In accordance with the invention there are provided new compounds of formula I,

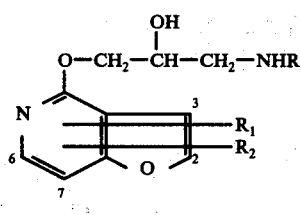

wherein
R is alkyl of 3 to 7 carbon atoms or cycloalkyl of 3 to 7 carbon atoms, cycloalkyl of 3 to 7 carbon atoms monosubstituted by alkyl of 1 to 4 carbon atoms, α-dialkylpropyinyl of 5 to 9 carbon atoms or α-dialkyl-allyl of 5 to 9 carbon atoms, hydroxyalkyl of 2 to 7 carbon atoms or phenoxyalkyl of 8 to 11 carbon atoms, the oxygen atom of the last two radicals being separated by at least two carbon atoms from the nitrogen atom to which R is bound,
$R_1$ is
  i. hydrogen or alkyl of 1 to 4 carbon atoms in the 2,3,6 or 7 position, or
  ii. chlorine or bromine, in the 2, 3 or 7 position,
  iii. nitro or -NHA wherein A is alkanoyl of 1 to 4 carbon atoms, in the 2, 3 or 7 position, or
  iv. fluorine, cyano or COOB, wherein B is alkyl of 1 to 4 carbon atoms in the 2 or 3 position, and
$R_2$ is
  i. hydrogen or alkyl of 1 to 4 carbon atoms in the 2, 3, 6 or 7 position, or
  ii. chlorine or bromine, in the 2, 3 or 7 position, or
  iii. fluorine in the 2 or 3 position.

When R is alkyl or hydroxyalkyl the alkyl moiety thereof preferably is branched, especially in an α-position to the nitrogen atom to which it is bound. Especially preferred alkyl radicals are isopropyl, tert. butyl, 3-pentyl and tert. pentyl (α-dimethylpropyl). The preferred hydroxyalkyl radicals are, for example, the α-dimethylhydroxyethyl and α-dimethylhydroxypropyl groups.

When R contains cycloalkyl, this especially signifies cyclopropyl, cyclopentyl or cyclohexyl.

When R is cycloalkyl monosubstituted by alkyl, the alkyl substituent thereof especially signifies methyl. The alkyl substituent is conveniently in the α-position. A preferred alkylcycloalkyl group is 1-methylcyclohexyl.

When R is the α-dialkylpropinyl or α-dialkylallyl defined above, the alkyl groups thereof preferably are identical and specially signify methyl.

When R is the phenoxyalkyl radical defined above, this especially signifies phenoxyethyl.

R especially signifies the phenoxyalkyl, α-dialkylpropynyl or alkyl group defined above; the two latter significances are specially preferred.

When $R_1$ and/or $R_2$ is alkyl of 1 to 4 carbon atoms, these radicals especially contain 1 or 2, preferably 1 carbon atom.

$R_1$ preferably signifies hydrogen, bromine, chlorine, cyano or the alkyl group defined above; the two latter substituents are especially preferred.

$R_2$ specially signifies hydrogen or the alkyl group defined above.

A preferably signifies formyl or acetyl.
B preferably signifies methyl, ethyl or tert.butyl.
$R_1$ preferably is in the 2 or 3 position, especially the 2 position. $R_2$ preferably is in the 7 position.

Further, in accordance with the invention a compound of formula I may be obtained by a process comprising a. hydrolyzing the oxazolidine group in a compound of formula II,

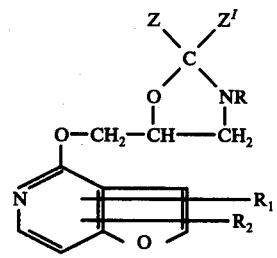

wherein R, $R_1$ and $R_2$ are as defined above, and

is a radical capable of being split off hydrolytically,
or b. substituting in the 4 position a compound of formula III,

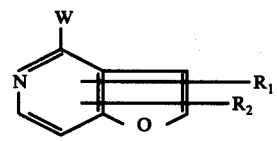

wherein $R_1$ and $R_2$ are as defined above, and W is an anionic leaving group, by reaction with a compound of formula V,

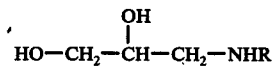

wherein R is as defined above.

The processes of the invention may be carried out in accordance with known methods.

Process variant a) is a hydrolysis of an oxazolidine. Oxazolidines are readily hydrolyzable (see Chemical Reviews 53, 315–317 [1953]). Therefore, Z and $Z^I$ in the compounds of formula II may signify the radical of any desired aliphatic or aromatic aldehyde or ketone

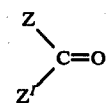

, e.g. of propionaldehyde, benzaldehyde, acetaldehyde or acetone. The hydrolysis of compounds of formula II is conveniently effected under acid conditions. A dilute acid, especially a mineral acid, e.g. 0.5 N to 3 N hydrochloric acid or 1 N sulphuric acid, is preferably chosen as suitable acid. The reaction may be effected in the presence of water. It is possible to use a water-miscible organic solvent, e.g. a lower alkanol such as ethanol, but this is not essential. The reaction temperature may vary, e.g., between 0° and about 80° C, and is preferably effected at an elevated temperature, e.g. 60° to 80° C.

Process variant b) is a substitution reaction on an aromatic, nitrogen-containing heterocycle which contains an anionic leaving group on a carbon atom adjacent to the nitrogen. W preferably signifies chlorine, bromine or a lower alkylthio group such as methylthio; W especially signifies chlorine. The substitution is readily effected, e.g. by allowing to stand a solution of a compound of formula III and a compound of formula V. This is effected in an inert organic solvent, e.g. a lower alkanol such as tert. butanol. The reaction is preferably effected in the presence of a base, e.g. an alkali metal alcoholate such as potassium tert.butylate. The reaction temperature may vary between about 0° and approximately 80° C, and is preferably effected at room temperature. The reaction may be accelerated by stirring.

Acid addition salt forms of compound of formula I, e.g. the hydrochloride, hydrogen malonate, fumarate, hydrogen fumarae, hydrogen maleate, or naphthalene-1,5-disulphonate may be produced in known manner from the free base forms, and vice versa.

Some of the compounds of formula III are known (F. Eloy and A. Deryckere, Helv.chem.Acta 53, 645–647 [1970]; and E. Bisagni et al., Bull.Soc.Chim.France 1974, 515–518).

The compounds of formula IIIa,

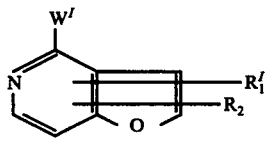

wherein
R$_2$ is as defined above,
W$^1$ is chlorine or bromine, and
R$_1^I$ is hydrogen or an alkyl group of 1 to 4 carbon atoms in the 2, 3, 6 or 7 position, a chlorine or bromine atom in the 2, 3 or 7 position, a nitro group in the 7 position, or a group of the series fluorine, cyano or COOB, wherein B is as defined above, in the 2 or 3 position, are obtained, for example, by treating a compound of formula IV,

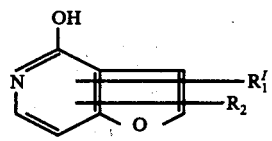

wherein R$_1^I$ and R$_2$ are as defined above, with phosphorus oxychloride or phosphorus oxybromide.

In one convenient method of producing nitro compounds of formula III a corresponding compound of formula III wherein positions 2 and 3 are unsubstituted is nitrated in conventional manner. It is expected that any conventional nitrating agent will attack position 2 rather than position 3 so the resulting compound of formula III would be expected to be the 2-nitro derivative.

Any nitro group in the compounds of formula III may be converted into amino or an NHA group. A 4-chloro substituent may be converted into an alkylthio group in conventional manner.

The compounds of formula IVa,

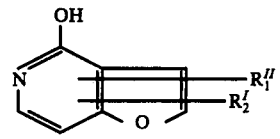

wherein
R$_1^{II}$ and R$_2^I$ are independently hydrogen, alkyl of 1 to 4 carbon atoms in the 2, 3, 6 or 7 position, or a member of the series fluorine, chlorine or bromine in the 2 or 3 position, may be obtained by a Curtius degradation — via the vinylisocyanates formed in situ — of the corresponding 2-furylacrylic acid azides.

If desired, in the compounds of formula IVa a chlorine, bromine or nitro substituent in the 7 position may be introduced by chlorination, bromination or nitration. A bromine atom in the 2 or 3 position may be substituted by a cyano group and this cyano group may be converted by alcoholysis into a COOB group, wherein B is as defined above.

These measures may be carried out in accordance with known methods, have been described in the literature and are partially described in the experimental part.

Insofar as the production of the starting materials is not described, these are known or may be produced in accordance with known processes, or in a manner analogous to the processes described herein or to known processes.

Individual optical isomer forms may be obtained from racemic forms in conventional manner. In one convenient preparation a compound of formula I is obtained in optically active form starting from optically pure R or S glyceraldehyde.

In the following non limitative Examples all temperatures are indicated in degrees Centrigrade and are uncorrected.

The nitro or acetamido substituent of the compounds of formula I can be either in the 2 or 3 position of the nucleus; is probably in the 2 position; it is in the same position as the nitro substituent in the mono-nitro derivative obtained by nitrating 4-chloro-furo-[3,2-c]-pyridine in the presence of nitric and sulphuric acids.

EXAMPLE 1:
1-isopropylamino-3-(4-furo-[3,2-c]pyridinyloxy)-2-propanol

[process variant a)]

2.0 g of 4-(3-isopropyl-2-phenyl-5-oxazolidinylmethoxy)-furo[3,2-c]pyridine in 15 cc of 1 N hydrochloric acid are heated to 70° for ½ hour, extraction is effected with ether, and the aqueous phase is made alkaline with solid potassium carbonate. Extraction is effected with ether, the ether solution is dried over magnesium sulphate and concentrated (M.P. of the hydrogen maleate form 139° –140° ).

The 4-(3-isopropyl-2-phenyl-5-oxazolidinyl-methoxy)-furo[3,2-c]pyridine, used as starting material, is obtained as follows:

The 4-hydroxyfuro[3,2-c]pyridine (M.P. 196°–198°) is obtained by conversion of 3-(2-furyl)acrylic acid with thionyl chloride into its chloride, conversion of the chloride into 3-(2-furyl) acrylic acid azide by reacting it with sodium azide at 0°, and refluxing 3-(2-furyl)acrylic acid azide in diphenyl ether (240°). The 4-hydroxyfuro[3,2-c]pyridine yields 4-chloro-furo[3,2-c]pyridine by reaction with phosphorus oxychloride. After reacting this compound with 3-isopropyl-2-phenyl-5-hydroxymethyloxazolidine in the presence of potassium tert.butylate, 4-(3-isopropyl-2-phenyl-5-oxazolidinylmethoxy)-furo[3,2-c]pyridine is obtained as an oil.

The 3-isopropyl-2-phenyl-5-hydroxymethyloxazolidine (B.P.$_{0.08}$ = 133°–134°) is obtained by converting 1,2-dihydroxy-3-chloropropane at 100° with an excess (15 ×) of isopropylamine into 1,2-dihydroxy-3-isopropylaminopropane (B.P.$_{0.4}$ = 96°–98°) and refluxing the 1,2-dihydroxy-3-isopropylaminopropane with an excess of benzaldehyde in benzene.

EXAMPLE 2:
1-isopropylamino-3-(4-furo[3,2-c]pyridinyl-oxy)-2-propanol

[process ariant b)]

0.54 g of potassium are dissolved with heating in 60 cc of tert.butanol. After cooling, 1.84 g of 1-isopropylamino-2,3-dihydroxypropane are added and subsequently 2.1 g of 4-chloro-furo[3,2-c]pyridine are added. After stirring for one day at room temperature, heating is effected to 50° for a further day. The reaction solution is concentrated in a vacuum, the residue is taken up in 1 N hydrochloric acid and ether, the aqueous phase is neutralized with 2 N soda solution and extracted with methylene chloride. After drying over magnesium sulphate and concentrating, the title compound is obtained as an oil, which yields the hydrogen maleate having an M.P. of 139°–140°, with maleic acid in tetrahydrofuran.

The 1-isopropylamino-2,3-dihydroxypropane, used as starting material, is obtained by reacting glycidol with an equivalent amount of isopropylamine in ethanol.

The following compounds of formula I are obtained in a manner analogous to Examples 1 and 2, using the corresponding starting materials of formula II, wherein

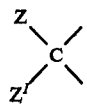

signifies

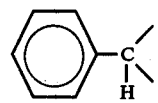

[process variant a)], or of formula III, wherein W is chlorine [process variant b)]:

| Ex.Nr. | R | R$_1$ | R$_2$ | Salt form | M.P. |
|---|---|---|---|---|---|
| 3 | Isopropyl | 2-Methyl | H | | 73–74° |
| 4 | Isopropyl | 6-Methyl | H | | 73–75° |
| 5 | tert.Butyl | H | H | Hm[1] | 165–168° |
| 6 | tert.Butyl | 2-Methyl | H | Hf[2] | 196–197° |
| 7 | tert.Butyl | 7-Chloro | H | Hf[2] | 154–157° |
| 8 | tert.Butyl | 3-Carbethoxy | 2-Methyl | | B) |
| 9 | Cyclopropyl | 7-NHCO(CH$_2$)$_3$CH$_3$ | H | | |
| 10 | 1-n-butyl-cyclopropyl | 7-NHCHO | H | | |
| 11 | α-di-n-propyl-propinyl | 2-cyano | H | | A) |
| 12 | 1-methyl-cycloheptyl | 7-nitro- | 3-methyl | | |
| 13 | α-di-ethyl-allyl | 2-methyl | 6-n-butyl | | |
| 14 | cycloheptyl | 7-n-butyl | H | | |
| 15 | 3-hydroxy-propyl | H | H | | |
| 16 | α-di-ethyl-hydroxyethyl | H | H | | |
| 17 | phenoxypropyl | 2-F | 7-isopropyl | | |
| 18 | α-dimethyl-phenoxyethyl | 3-methyl | 7-Br | | |

[1] Hm = Hydogen maleate
[2] Hf = Hydrogen fumarate

A. The corresponding 4-hydroxy-2-carbonitrile or 4-hydroxy-3-carbonitrile derivative, required as starting material of formula IV, may be obtained by heating under reflux the 2-bromo- or 3-bromo-4-hydroxy derivative of formula IV with CuCN in dimethyl formamide, concentrating the solution in a vacuum, pouring into a heated solution of potassium cyanide in H$_2$O, and after standing at 50° for 1 hour, extracting with methylene chloride.

B. The corresponding 4-hydroxy-2-carboxylic acid ester or 4-hydroxy-3-carboxylic acid ester, required as starting material of formula IV, may be obtained by boiling the corresponding 4-hydroxy-2-carbonitrile or 4-hydroxy-3-carbonitrile derivative of formula IV under reflux in the corresponding alkanol and passing HCl gas through the reaction solution.

The compounds of formula I are useful because they possess pharmacological activity in animals. In particular, the compounds of formula I are useful as adrenergic β-blocking agents, e.g. for the prophylaxis and therapy of coronary diseases, particularly in the treatment of Angina pectoris, in the hyperkinetic heart syndrome and conditions resulting from muscular hypertrophic subvalvular aortic stenosis, as indicated in standard tests, e.g. by an inhibition of the positive inotropic adrenaline effect in the spontaneously beating guinea pig atrium at a bath concentration of from 0.005 to 2.5 mg/litre, in accordance with the method of K. Sammel;

Helv. Physiol. Acta. 25 CR 215-221 (1967), and an inhibition of the tachycardia and hypotension caused by isoproterenol [1-(3,4-dihydroxyphenyl)-2- isopropylaminoethanol] in the infusion test in the anaesthetized dog at an effective cumulative dose of from 0.02 to 0.6 mg/kg animal body weight, administered intraveneously by infusion.

For the above-mentioned use, the dosage administered will, of course, vary depending on the compound employed, mode of administration and treatment desired. However, in general, satisfactory results are obtained with a daily dosage of from about 0.01 to 10, e.g. 0.1 to 10, mg/kg animal body weight, conveniently given in divided doses 2 to 4 times a day or in sustained release form. For the larger mammal, the total daily dosage is in the range of from about 2 to 700, e.g. 2 to 100 or 7 to 700, mg, and dosage forms suitable for oral administration comprise from about 0.5 to 350 mg of the compound, admixed with a solid or liquid pharmaceutical carrier or diluent.

Preferred total daily dosages are from 2 to 100 mg and a preferred unit dosage contains from 0.5 to 50 mg of the compound.

The compounds of formula I are furthermore particularly useful as inhibitors of hyperlipoidemia induced by emotional stress and also as agents for the treatment or prophylaxis of myocardism as indicated in standard tests for showing inhibition of increased free fatty acid concentration due to mobilisation, and lipolysis, in blood induced by emotional stress, for example, by an inhibition of glycerol release stimulated by isoproterenol i) in vitro, e.g. at a concentration of about 0.1 to about 10 mg/l solution of the compounds in fat cells of the epididymal fat tissue of rats, the cells having been isolated in accordance with the method of M. Rodbell [J. biol. chem. 239, 375-80 (1964)], and ii) in vivo, e.g. in rats on s.c. administration of from about 0.1 to about 1 mg/kg animal body weight of the compounds.

The compounds of formula I are furthermore useful as inhibitors of hyperglycemia induced by emotional stress and therefore as suppressants of appetite induced by emotional stress, as indicated in standard tests, e.g. by an inhibition of glucose release stimulated by isoproterenol in rats in vivo on s.c. administration of from about 0.1 to about 10 mg/kg of animal body weight of the compounds.

For the above-mentioned uses for stress conditions the dosage will, of course, vary depending on the compound employed, mode of administration and treatment desired. However, in general, satisfactory results are obtained with a daily dosage of from about 0.01 to about 5 mg/kg animal body weight, conveniently given in divided doses 2 to 4 times a day or in sustained release form. For the larger mammal, the total daily dosage is in the range from about 1 to about 700, e.g. 1 to 300 or 7 to 700, mg, and dosage forms suitable for oral administration comprise from about 0.25 to about 150 or 2 to 350 mg of the compounds admixed with a solid or liquid pharmaceutical carrier or diluent.

Preferred total daily dosages are from 7 to 700 mg and a preferred unit dosage contains from 2 to 350 mg of the compound.

The compounds of formula I are furthermore particularly useful as anti-arrhythmic agents, e.g. for the treatment of heart rhythm disorders, as indicated in standard tests, for example by a protection against cardiac arryhthmia induced by chloroform in mice on i.p. administration of from 0.001 to 80 mg/kg animal body weight of the compounds in accordance with the principles of J. W. Lawson [J. Pharmacol. Exp. Therap. (1968) 160 22-31].

For this use the dosage will, of course, vary depending on the compound employed, mode of administration and treatment desired. However, in general, satisfactory results are obtained with a daily dosage of from about 0.01 mg to about 80, e.g. 0.1 to 10 or 0.01 to 10, mg/kg animal body weight, conveniently given in divided doses 2 to 4 times a day or in sustained release form. For the larger mammal, the total daily dosage is in the range from about 1 to about 700, e.g. 1 to 100 or 7 to 700, mg, and dosage forms suitable for oral administration comprise from about 0.2 to about 350 mg of the compounds admixed with a solid or liquid pharmaceutical carrier or diluent.

Preferred total daily dosages are from 7 to 700 mg and a preferred unit dosage contains from 2 to 350 mg of the compound.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

Preferred compounds are compounds of formula Iw

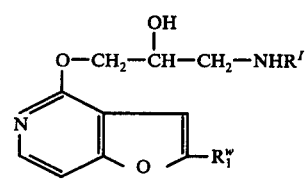

wherein

R$^I$ is a branched alkyl radical in an α position to the nitrogen atom to which R$^I$ is bound, and R$_1^W$ is cyano, bromine or alkyl to 1 to 4 carbon atoms.

In another preferred group R$_1$ is hydrogen, alkyl, preferably methyl, in the 2 position, or chlorine, bromine or cyano in the 2 or 3 position and R$_2$ is hydrogen or alkyl, preferably methyl, in the 7 position.

When R is hydroxyalkyl or phenoxyalkyl, the hydroxy or phenoxy radical is conveniently in the omega position of the alkyl moiety. The number of carbon atoms referred to above with regard to α-dialkylpropynyl, α-dialkyl-allyl, phenoxyalkyl and alkanoyl is the total number of carbon atoms in the whole radical. Conveniently R$_1$ is other than nitro in the 2 or 3 position. Compounds of formula I having the S configuration are especially active in the emotional stress indication mentioned above.

We claim:

1. A racemic or optically active compound of formula I,

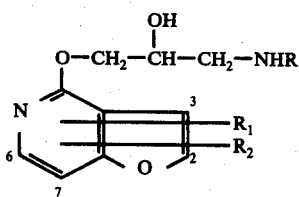

wherein
R is alkyl of 3 to 7 carbon atoms or cycloalkyl of 3 to 7 carbon atoms, cycloalkyl of 3 to 7 carbon atoms monosubstituted by alkyl of 1 to 4 carbon atoms, α-dialkylpropynyl of 5 to 9 carbon atoms or α-dialkyl-allyl of 5 to 9 carbon atoms, hydroxyalkyl of 2 to 7 carbon atoms or phenoxyalkyl of 8 to 11 carbon atoms, the oxygen atom of the last two radicals being separated by at least two carbon atoms from the nitrogen atom to which R is bound, $R_1$ is
i. hydrogen or alkyl of 1 to 4 carbon atoms, in the 2,3,6 or 7 position, or
ii. chlorine or bromine, in the 2, 3 or 7 position,
iii. nitro or-NHA wherein A is alkanoyl of 1 to 4 carbon atoms, in the 2, 3 or 7 position, or
iv. fluorine, cyano or COOB, wherein B is alkyl of 1 to 4 carbon atoms, in the 2 or 3 position, and $R_2$ is
i. hydrogen or alkyl of 1 to 4 carbon atoms in the 2, 3, 6 or 7 position,
ii. chlorine or bromine, in the 2, 3 or 7 position, or
iii. fluorine in the 2 or 3 position, or a pharmaceutically acceptable acid addition salt thereof.

2. A method of treating Angina pectoris, hyperkinetic heart syndrome and conditions resulting from muscular hypertrophic subvalvular aortic stenosis in animals which comprises administering to an anima in need of such treatment a therapeutically effective amount of a compound of claim 1.

3. A method of treating heart rhythm disorders in animals which comprises administering to an animal in need of such treatment a therapeutically effective amount of a compound of claim 1.

4. A method of treating hyperlipoidemiaor hyperglycemia in animals under stress which comprises administering to an animal in need of such treatment a therapeutically effective amount of a compound of claim 1.

5. A compound of claim 1 wherein $R_2$ is H.

6. A compound of claim where R is other than phenoxy-alkyl, $R_1$ is hydrogen or alkyl in the 2, 3, 6 or 7 position, or chlorine or bromine in the 2, 3 or 7 position, or fluorine, cyano or COOB wherein B is alkyl of 1 to 4 carbon atoms, in the 2 or 3 position, or nitro in the 7 position.

7. A pharmaceutical composition comprising an effective amount of a compound according to claim 1 in association with a pharmaceutical carrier or diluent.

8. The compound of claim 1 where R, $R_1$ and $R_2$ are, respectively, isopropyl, H and H.

9. The compound of claim 1 where R, $R_1$ and $R_2$ are, respectively, isopropyl, 2-methyl and H.

10. The compound of claim 1 where R, $R_1$ and $R_2$ are, respectively, isopropyl, 6-methyl and H.

11. The compound of claim 1 where R, $R_1$ and $R_2$ are, respectively, tert.butyl, H and H.

12. The compound of claim 1 where R, $R_1$ and $R_2$ are, respectively, tert.butyl, 2-methyl and H.

13. The compound of claim 1 where R, $R_1$ and $R_2$ are, respectively, tert.butyl, 7-chloro and H.

14. The compound of claim 1 where R, $R_1$ and $R_2$ are, respectively, tert.butyl, 3-carbethoxy and 2-methyl.

* * * * *